United States Patent [19]
Vartuli et al.

[11] 4,247,419
[45] Jan. 27, 1981

[54] SINGLE PHASE VANADIUM(IV)BIS(METAPHOSPHATE) OXIDATION CATALYST WITH IMPROVED INTRINSIC SURFACE AREA

[75] Inventors: James C. Vartuli, West Chester, Pa.; Lee R. Zehner, Dublin, Ohio

[73] Assignee: Atlantic Richfield Company, Los Angeles, Calif.

[21] Appl. No.: 102,818

[22] Filed: Dec. 13, 1979

[51] Int. Cl.$^3$ .................. B01J 27/14; B01J 31/02; B01J 27/02; C01B 15/16
[52] U.S. Cl. .................. 252/435; 252/437; 252/430; 252/440; 423/314
[58] Field of Search .............. 252/435, 437, 430, 440; 423/314

[56] References Cited

U.S. PATENT DOCUMENTS

| | | | |
|---|---|---|---|
| 3,031,508 | 4/1962 | Etherington et al. | 252/437 X |
| 3,293,268 | 12/1966 | Bergman et al. | 252/437 X |
| 3,977,998 | 8/1976 | Fuerker et al. | 252/435 |
| 4,043,943 | 8/1977 | Schneider | 252/435 X |
| 4,092,269 | 5/1978 | Mount et al. | 252/437 X |
| 4,165,299 | 8/1979 | Pedersen | 252/435 |
| 4,171,316 | 10/1979 | Pedersen | 252/437 X |

Primary Examiner—Delbert E. Gantz
Assistant Examiner—William G. Wright
Attorney, Agent, or Firm—Delbert E. McCaslin

[57] ABSTRACT

A method for the preparation of a single phase crystalline vanadium(IV)bis(metaphosphate), VO(PO$_3$)$_2$, catalyst having an improved intrinsic surface area of from about 5 to 15 m$^2$/g. and useful for the vapor phase oxidation of linear C$_4$ unsaturated olefins, such as n-butenes, to prepare maleic anhydride.

11 Claims, No Drawings

SINGLE PHASE VANADIUM(IV)BIS(METAPHOSPHATE) OXIDATION CATALYST WITH IMPROVED INTRINSIC SURFACE AREA

FIELD OF THE INVENTION

This invention is directed to a method for the preparation of a single phase vanadium(IV)bis(metaphosphate) catalyst having an increased intrinsic surface area and thus improved activity and selectivity for use in the preparation of maleic anhydride from unsaturated hydrocarbon feed.

BACKGROUND OF THE INVENTION

In the U.S Pat. No. 4,165,299, Aug. 21, 1979, there is disclosed a process for the preparation of a single phase vanadium(IV)bis(metaphosphate) catalyst for preparing maleic anhydride by the oxidation of unsaturated aliphatic hydrocarbons, which catalyst has an intrinsic surface area of from about 1.5 to 5.0 $m^2/g$., by forming a solid state mixture of vanadyl sulfate and phosphorus pentoxide and heating the mixture to a temperature of at least about 325° C. to liberate gases and form a vanadium phosphorus reaction product which product is cooled, washed with water, dried and calcined in air to form the catalyst.

A vanadium(IV)bis(metaphosphate) catalyst which has an intrinsic surface area of only 0.30 to 0.50 $m^2/g$. and the preparation thereof is also shown in an article by Bruce C. Tofield et al, J.C.S., Dalton Transactions, Part II, 1975, pp. 1806–1810 and by G. Ladwig, Z. Chem., 1968, Vol. 8, p. 307, which after activation or conditioning is a good oxidation catalyst for unsaturated aliphatic hydrocarbons to produce maleic anhydride but suffers from a disadvantage of having a low intrinsic surface area. Such limited intrinsic surface area is generally undesirable because the activity of the oxides of vanadium and phosphorus are directly related to the intrinsic surface area, particularly when employed as oxidation catalysts to prepare maleic anhydride.

The typical prior art phosphorus-vanadium-oxygen catalyst systems are generally prepared by reducing vanadium pentoxide to vanadium(IV) in water or an organic solvent with hydrochloric acid or other suitable reducing agent. A source of phosphorus, usually phosphoric acid, is mixed with the vanadium (IV) solution to produce a catalyst precursor which is heat treated to give the production catalyst.

U.S. Pat. No. 4,062,873 and the numerous patent references noted therein all of which are deemed to be reiterated herein, describe various vanadium-phosphorus oxide catalyst systems employed in producing maleic anhydride.

U.S. Pat. No. 3,864,280 describes a crystalline phosphorus-vanadium mixed oxide hydrocarbon oxidation catalyst composition consisting primarily of pentavalent phosphorus, vanadium and oxygen.

SUMMARY OF THE INVENTION

According to the present invention there is provided a novel method for preparing a single phase vanadium-(IV)bis(metaphosphate), $VO(PO_3)_2$, catalyst, which method substantially increases the intrinsic surface area of the compound and improves the catalytic activity and selectivity for an air or oxygen partial oxidation of an unsaturated aliphatic hydrocarbon selected from 1-butene, 2-butene, and 1,3-butadiene or mixtures thereof at temperatures of from about 300° C. to 600° C. by contacting said hydrocarbon and air or oxygen with the vanadium(IV)-bis(metaphosphate), at contact times of from about 0.2 to 5 seconds of reactant feed over the compound, prepared by the instant method.

It is a primary object of this invention to provide a method for the preparation of a single phase crystalline vanadium(IV)bis(metaphosphate) useful as an oxidation catalyst to produce maleic anhydride and having a significantly improved intrinsic surface area.

It is another object of this invention to provide a novel type single phase vanadium(IV)bis(metaphosphate) catalyst having intrinsic surface area of from about 5 to 15.0 $m^2/g$, which provides yields of and selectivities to maleic anhydride at least equal to or higher than heretofore obtained by the oxidation of unsaturated aliphatic hydrocarbons.

These and other objects and advantages of this invention will become apparent from the description of the invention which follows and from the claims.

DESCRIPTION OF THE INVENTION

In accordance with the present invention, a single phase crystalline vanadium(IV)bis(metaphosphate), $VO(PO_3)_2$, compound is prepared by a novel method which improves the intrinsic surface area significantly as compared to known $VO(PO_3)_2$ catalyst preparation methods described in the aforementioned U.S. Pat. No. 4,165,299. The catalyst may be employed as an oxidation catalyst to produce maleic anhydride from 1-butene, 2-butene, and 1,3-butadiene or mixtures thereof under the activation and oxidation reaction conditions set forth herein and in the abovementioned U.S. Pat. No. 4,165,299.

The instant method for the preparation of the improved single phase vanadium(IV)bis(metaphosphate) oxidation catalyst compound having an intrinsic surface area of from about 5.0 to 15 $m^2/g$. involves a liquid phase reaction between vanadyl sulfate ($VOSO_4$), phosphorus pentoxide, and acetic anhydride with the liberation of exothermic heat. Excess liquid is generally decanted from the resulting slurry which is then subjected to a thermal treatment for a period sufficient for the liberation of gases and forming of a vanadium-phosphorus reaction product. However, the undecanted slurry may be thermally treated. The catalyst possesses a vanadium oxygen double bond and has a highly ordered structure. Stoichiometric amounts of the vanadyl sulfate and phosphorus pentoxide are generally employed in preparing the $VO(PO_3)_2$ compound but excess amounts of either compound may also be employed and the excess residue removed, by water washing, after reaction, to form the catalyst precursor. The liquid phase reaction is generally carried out at ambient temperatures e.g., 20° C. to 25° C. although higher or lower temperatures may be used. The thermal treatment will proceed at temperatures of at least 325° C. and temperatures as high as 475° C. or higher may be used to liberate the reaction gases. It is generally preferred to carry out the thermal treatment at a temperature of between about 400° C. and 460° C. to obtain a convenient rate of reaction.

The amount of acetic anhydride employed in the process of the invention can range from about 1 to 4 moles preferably 2 to 3 moles per mole of the combined vanadyl sulfate and phosphorus pentoxide present.

Greater amounts of acetic anhydride may be employed but generally are not required.

After preparation and water washing, the VO(PO$_3$)$_2$ compound is generally dried at 120° C., calcined in air at temperatures between about 450° C. and 500° C. or higher for at least two hours, then broken up and sieved to the appropriate Tyler Standard Sieve mesh size, usually for fixed bed reactor use. The resulting VO(PO$_3$)$_2$ compound (catalyst precursor) which has a surface area of approximately 5.0 to 15.0 m$^2$/g. requires a period of activation or conditioning for use in oxidizing the above indicated unsaturated aliphatic hydrocarbons. For the activation or conditioning the catalyst precursor is subjected to temperatures which are at or above the hydrocarbon oxidation reaction temperatures which are from about 300° C. to 600° C. preferably from 450° C. to 550° C., under a flow of from about 0.2 volume percent to about 2.0 volume percent preferably 0.5 to 1.5 volume percent in air of said hydrocarbon or mixture of hydrocarbons, to be oxidized and at an apparent contact time of from about 0.5 to 3.0 seconds, preferably 0.75 to 1.5 seconds for an appropriate period, to enable the hydrocarbon conversion to reach 90 percent or more, with subsequent temperature and flow rate adjustments to desired oxidation reaction conditions. Water vapor (steam) e.g., from about 10 to 35 mole percent, may be added to the reactant hydrocarbon gases during the activation period and subsequent oxidation reaction. The length of time required for activation or conditioning of the catalyst precursor and to permit the catalyst performance to become stabilized depends on the temperature employed and contact time of the hydrocarbon-air mixture but generally will be from about 4 to 8 hours. Apparent contact time calculated in seconds is equal to the flow rate of the hydrocarbon-air feed mixture at cc/second at reaction temperature and pressure, per cc of catalyst measured at ambient conditions. Once activated the VO(PO$_3$)$_2$ exhibits excellent performance as a catalyst for the oxidation of 1-butene, 2-butene and 1,3-butadiene, or mixtures thereof, to maleic anhydride for extended periods of time.

The VO(PO$_3$)$_2$ catalyst of this invention may also be prepared in the presence of a suitable carrier such as silica gel, aluminosilicates, alumina, silicon carbide and carbon to provide a support for the catalyst and thus a surface which gives physical strength and stability to the catalyst material as well as a surface area of up to 100 m$^2$/g. on the support.

The following examples are provided to illustrate the invention in accordance with the principles of this invention but are not to be considered as limiting the invention in any way except as indicated by the appended claims.

In the Examples which follow that are directed to unsaturated hydrocarbon oxidation employing the instant catalyst, the reactions were run in a 5/8 inch inside diameter stainless steel U-tube reactor which was immersed in a fluidized sand bath for maintaining the temperature of reaction. The lower half of the U-tube reactor was filled with catalyst having an 8-16 mesh (Standard Sieve). The VO(PO$_3$)$_2$ (precursor) catalyst is activated or conditioned in a stream of air with 1 volume percent of unsaturated hydrocarbon at a desired temperature for several hours at an appropriate apparent contact time over the catalyst. Following activation the temperature is decreased to the desired oxidation reaction temperature and the flow of hydrocarbon-air mixture, with or without the addition of steam, adjusted to the desired apparent contact time of between 0.5 to 3.0 seconds. The gaseous effluent oxidation reaction products from the reactor were passed through a series of water traps to adsorb the maleic anhydride and other by-products such as small amounts of acetic and acrylic acids; the maleic anhydride being converted to maleic acid in the aqueous solution. The gaseous effluent from the U-tube reactor was analyzed by InfraRed (I.R.) and gas chromatography to determine the concentration of carbon dioxide, carbon monoxide and any unconverted hydrocarbon. The aqueous solution containing the maleic acid was analyzed by gas chromatography to determine maleic anhydride yield and selectivity. Percent conversion of hydrocarbon and percent selectivity to maleic anhydride are calculated in mole percent.

EXAMPLE 1

Catalyst Preparation

A vanadium(IV)bis(metaphosphate) VO(PO$_3$)$_2$ catalyst was prepared as follows: 75.2 grams (0.461 mole) of vanadyl sulfate (VOSO$_4$) was added to 175 ml. of acetic anhydride at ambient temperature of 27° C. and stirred. 65.4 grams (0.461 mole) of phosphorus pentoxide (P$_2$O$_5$) was slowly added to the solution and was thoroughly mixed forming a slurry. Excess liquid was decanted from the slurry mixture and the resulting wet vanadyl sulfatephosphorus pentoxide product transferred to a furnace. The temperature of the furnace was increased at a rate of 1° C. per minute to a maximum of 450° C. and maintained for a period of sixteen hours liberating the reaction gases. After cooling the bluish green product was thoroughly washed with water to remove any soluble residues. After drying at 120° C. the product was calcined in air at 500° C. for two hours to give a VO(PO$_3$)$_2$ catalyst (precursor) having an intrinsic surface area of approximately 6.9 m$^2$/g. The oxidation state of the vanadium was determined to be +4.0 by permanganate titration. After calcination the vanadium-(IV)bis(metaphosphate) catalyst precursor was broken up (8–16 mesh size-Standard Sieve) for use after activation or conditioning, in the oxidation of 1-butene, 2-butene and 1,3-butadiene to maleic anhydride.

EXAMPLE 2

Catalyst Preparation

The procedure of Example 1 was carried out employing 75.2 g. VOSO$_4$, 175 ml. of acetic anhydride and 65.4 g. of P$_2$O$_5$. Excess liquid was decanted and the resulting vanadyl sulfate-phosphorus pentoxide product heated in the furnace at 1° C. per minute to a maximum of 400° C. giving a VO(PO$_3$)$_2$ catalyst (precursor) with an intrinsic surface area of approximately 5.6 m$^2$/g.

EXAMPLE 3

Catalyst Preparation

The procedure of Example 1 was repeated employing 75.2 g. of VOSO$_4$, 65.4 g. of P$_2$O$_5$ and 250 ml. of acetic anhydride. The decanted vanadyl sulfate-phosphorus pentoxide product was heated at a rate of 1° C. per minute to a maximum of 450° C. giving an analysis of VO(PO$_3$)$_2$ catalyst (precursor) with an intrinsic surface area of approximately 13.2 m$^2$/g.

EXAMPLE 4

Catalyst Preparation (Supported)

75.2 g. of VOSO$_4$ was added to 250 ml. of acetic anhydride along with 90.0 g. of SiO$_2$-Al$_2$O$_3$ with stirring. 65.43 g. of P$_2$O$_5$ was slowly added to the solution which was thoroughly mixed. Excess liquid was decanted and the resulting mixture heated in a furnace at a rate of 1° C. per minute to a maximum temperature of 450° C. and maintained for a period of 12 hours liberating the reaction gases. After cooling the product was thoroughly washed with water to remove any soluble residue and dried at a temperature of 120° C. The dried product was calcined in air at 500° C. for 2 hours giving an SiO$_2$-Al$_2$O$_3$ supported VO(PO$_3$)$_2$ catalyst precursor having an intrinsic surface area of 28.0 m$^2$/g.

EXAMPLE 5

A number of runs were made employing 30 ml of the vanadium(IV)bis(metaphosphate) of Example 1 loaded into the lower half of the U-tube reactor which was immersed in a fluidized sand bath. The catalyst (precursor) was activated in a stream of air and 1 volume percent of 1-butene at 490° C. for 16 hours at an apparent contact time of approximately 3.0 seconds. Following conditioning of the catalyst the reaction temperature was decreased to the desired temperature and the apparent contact time adjusted to desired conditions. Steam was added to the reactions system. Results giving conversions and selectivities are tabulated in Table 1 below.

TABLE 1

| Run No. | Contact Time (sec.) | Temp. °C. | Mole % Steam | Mole %[1] Conversion | Mole %[2] Selectivity to Maleic Anhydride |
|---|---|---|---|---|---|
| 1 | 1.02 | 368 | 29.4 | 79 | 68.2 |
| 2 | 0.73 | 412 | 22.6 | 87 | 67.6 |
| 3 | 0.69 | 461 | 17.6 | 100 | 66.8 |
| 4 | 0.48 | 491 | 18.0 | 100 | 55.6 |

[1]% conversion determined by gas chromatograph analyses of C$_4$ in effluent gas.
[2]% selectivity to maleic anhydride determined by gas chromatography analysis.

EXAMPLE 6

The procedure of Example 5 was repeated employing 30 ml of the vanadium(IV)bis(metaphosphate) of Example 3. The catalyst (precursor) was activated in a stream of air and 1 volume percent of 1,3-butadiene at 510° C. for five hours at an apparent contact time of 3.0 seconds. Following conditioning of the catalyst the reaction temperature was decreased to the desired temperature and the apparent contact time adjusted to desired conditions. Steam was added to the reaction system. Results giving conversions and selectivities are tabulated in Table 2 below.

TABLE 2

| Run No. | Contact Time (sec.) | Temp. °C. | Mole % Steam | Mole %[1] Conversion | Mole %[2] Selectivity to Maleic Anhydride |
|---|---|---|---|---|---|
| 1 | 1.50 | 400 | 20.5 | 97 | 66.5 |
| 2 | 0.75 | 430 | 18.5 | 100 | 67.8 |

[1]% conversion determined by gas chromatograph analyses of C$_4$ in effluent gas.
[2]% selectivity to maleic anhydride determined by gas chromatography analysis.

The higher intrinsic surface area VO(PO$_3$)$_2$ catalyst proved to be a good catalyst for the oxidation of normal, unsaturated C$_4$ hydrocarbons to maleic anhydride. The higher surface area somewhat improved the activity of the catalyst. X-ray analysis (powder diffraction patterns) of the freshly prepared and activated VO(PO$_3$)$_2$ catalyst and a catalyst which had been on stream for over 400 hours in the presence of from 5 to 30 mole percent steam were identical with no noticeable deterioration.

We claim:

1. A method for the preparation of a single phase crystalline vanadium(IV)bis(metaphosphate) oxidation catalyst for preparing maleic anhydride by oxidation of unsaturated aliphatic hydrocarbons, which catalyst has an intrinsic surface area of from about 5.0 to 15.0 m$^2$/g., which comprises the steps of:
    forming a slurry of vanadyl sulfate, acetic anhydride and phosphorus pentoxide with the liberation of exothermic heat;
    introducing said slurry into a heating zone and maintaining said zone at a temperature of at least about 325° C. for a period sufficient for the liberation of gases and forming a vanadium phosphorus reaction product;
    cooling the reaction product and washing with water to essentially remove any soluble residue;
    drying the washed product and calcining in air to obtain a single phase crystalline vanadium(IV)bis(metaphosphate) catalyst having an intrinsic surface area of from about 5.0 to 15.0 m$^2$/g.

2. A method according to claim 1 wherein the slurry is formed at ambient temperatures.

3. A method according to claim 1 wherein at least stoichiometric amounts of vanadyl sulfate and phosphorus pentoxide are employed to form the slurry.

4. A method according to claim 1 wherein the amount of acetic anhydride employed is in the range of from about 1 to 4 mole per mole of the combined vanadyl sulfate and phosphorus pentoxide present.

5. A method according to claim 1 wherein excess liquid is decanted from said slurry prior to introduction into the heating zone.

6. A method according to claim 1 wherein the slurry of vanadyl sulfate, phosphorus pentoxide and acetic anhydride is reacted at a temperature of between about 400° C. and 460° C.

7. A method according to claim 1 wherein the reaction product is dried at a temperature of about 120° C. and calcined in air at a temperature of at least 450° C.

8. A method according to claim 1 wherein the single phase crystalline vanadium(IV)bis(metaphosphate) catalyst is prepared in the presence of a suitable carrier or support material.

9. A method according to claim 4 wherein the amount of acetic anhydride employed is between about 2 to 3 moles.

10. A method according to claim 8 wherein the carrier or support material is added to the vanadyl sulfate, acetic anhydride, phosphorus pentoxide slurry.

11. A method according to claim 10 wherein the carrier or support is an aluminosilicate.

* * * * *